United States Patent [19]
Thornton et al.

[11] Patent Number: 5,770,150
[45] Date of Patent: Jun. 23, 1998

[54] TEST KIT FOR THE QUALITATIVE DETERMINATION OF PEROXIDES IN FAT

[75] Inventors: Gregory Lee Thornton, West Des Moines; Lawrence Keith Schlatter, Ankeny; Douglas Howard Catron, Des Moines, all of Iowa

[73] Assignee: Kemin Industries, Inc., Des Moines, Iowa

[21] Appl. No.: 873,359

[22] Filed: Jun. 12, 1997

Related U.S. Application Data

[62] Division of Ser. No. 542,937, Oct. 13, 1995, Pat. No. 5,670,374.

[51] Int. Cl.$^6$ .................................................. G01N 33/06
[52] U.S. Cl. ............................ 422/61; 422/68.1; 422/75; 422/55; 422/102; 436/20; 436/23; 436/60
[58] Field of Search ............................. 422/61, 68.1, 75, 422/102, 55; 436/20, 23, 60

[56] References Cited

U.S. PATENT DOCUMENTS

| | | | |
|---|---|---|---|
| 4,098,575 | 7/1978 | Matsushita | 436/20 |
| 4,444,193 | 4/1984 | Fogt et al. | 128/632 |
| 4,471,055 | 9/1984 | Opp | 422/128 |
| 4,731,332 | 3/1988 | Blumenthal et al. | 436/61 |
| 5,055,410 | 10/1991 | Blumenthal et al. | 436/60 |
| 5,480,808 | 1/1996 | Kauffman et al. | 436/135 |
| 5,670,374 | 9/1997 | Thornton et al. | 436/23 |

OTHER PUBLICATIONS

Takeshita et al. Study on improving the determination of peroxide value acetic acid–isooctane method. II Koko-shiken, Daigaku Kogukubu Kiyo, 27, 18–24 Abstract only, 1994.

Hare et al. "Modified potentiometric method with isooctane for peroxide value determination". Yakegaku, 43(1), 18–22 Abstract only, 1994.

Tenhunen, Esko A comparison of some methods for determination of peroxides in 1,3–butadiene. Finn. Chem. Lett. (1976), 7, 167–9; Abstract only, 1976.

Takeshita et al. "Determination of peroxide value by acetic acid–isooctane method". Yukagaku, 43 (7), 586–93, Abstract only, 1994.

Al–Kahtani, J. Amer. Oil Chemists' Soc., 68(11):857–862(Nov. 1991).

Matsushita and Asakawa, Chap. 11 in *Autoxidation in Food and Biological Systems*, M. Simic and M. Karel, eds., Plenum Press (New York: 1980), pp. 185–190.

Gray,*J. Amer. Oil Chemists' Soc.*,55: 539–546(Jun. 1978).

AOCS Recommended Practice Cd 8b–90, *Sampling and Analysis of Commercial Fats and Oils*, (Assoc. Off. Anal. Chem: 1993).

AOAC Official Methods of Analysis, p. 956 (Assoc. Off. Anal. Chem: 1990).

HACH package insert for "Hydrogen Peroxide Test Kit, Model HYP–1, Cat. No. 22917–00".

Uchiyana et al. CA abstract No. 113:189859 from *Electroanalysis*, 1990, vol. 2(3), pp. 259–261.

Derwent WPIDS abstract No. 78–32675A—From JP 53030388A, 1978.

*Primary Examiner*—Jill Warden
*Assistant Examiner*—Sharidan Carrillo
*Attorney, Agent, or Firm*—Welsh & Katz, Ltd.

[57] ABSTRACT

A process and test kit for the rapid qualitative determination of fat oxidation based on an iodometric method for peroxide value and employing ready-made test solutions is disclosed. A visible color change is used to determine whether a fat sample contains an amount of fat peroxides in excess of a predetermined amount, and is therefore unacceptable.

5 Claims, 1 Drawing Sheet

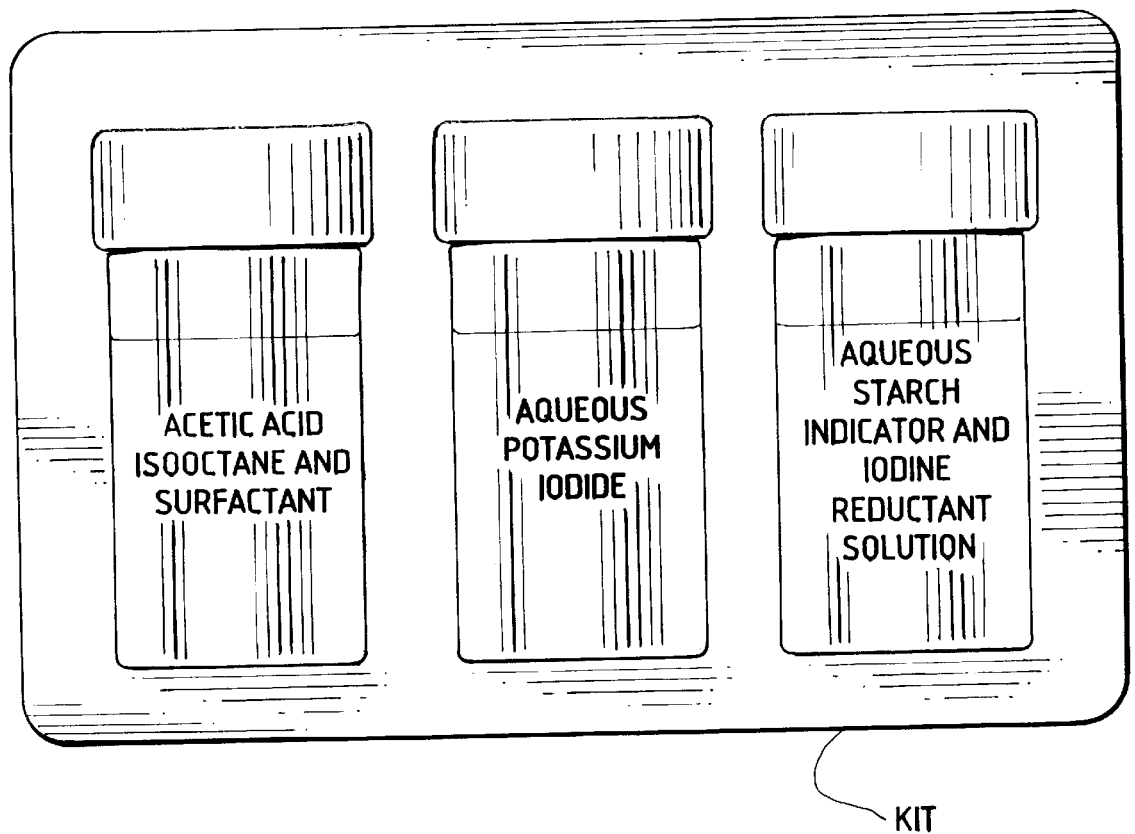

TEST KIT FOR THE QUALITATIVE DETERMINATION OF PEROXIDES IN FAT

This is a division of application Ser. No. 08/542,937, filed Oct. 13, 1995, now U.S. Pat. No. 5,670,374.

DESCRIPTION

1. Technical Field

The present invention relates to a quick and simple process and test kit for the qualitative determination of the presence of oxidized fat based on the iodometric method for peroxide value.

2. Background of the Invention

Fats and oils are solid and liquid triglyceride esters, respectively, that are frequently used in human foods and animal feeds. These triglycerides are usually collectively referred to herein as fats. Edible oils and fats are commonly used by processors of human foods. Animal fat obtained from rendering plants that is not suitable for human consumption is often used by animal feed processors.

Because fats are subject to oxidation and resultant rancidity, oils and fats should be evaluated upon receipt by either processor to determine rancidity. Although laboratory tests are available to quantitatively determine fat oxidation, a rapid qualitative test is also desired by the food or feed processor to determine whether the fat contains an unacceptable level of oxidation products so that a fat shipment can be accepted or rejected at the loading dock or rail siding.

The primary products of fat oxidation are hydroperoxides that are generally referred to collectively as peroxides. Peroxides can subsequently react with other materials present in the fat to form lower molecular weight secondary products such as alcohols, aldehydes, free fatty acids and ketones.

The peroxide concentration in fat is conveniently expressed as the peroxide value (PV). Methods to determine the peroxide value are known and have been reviewed (Gray, 1978, *J. Amer. Oil Chem. Soc.*, 55: 539–546). However, the standard method used to determine the amount of peroxides in fat is the American Oil Chemists Society's (AOCS) peroxide value determination (AOCS Official Methods of Analysis, Cd 8b-90). The peroxide value found by this method is regarded as directly indicative of the degree of fat oxidation.

The peroxide value is the concentration of substances, in terms of milliequivalents of peroxide per 1000 grams of sample, that oxidize potassium iodide to iodine. In the procedure, potassium iodide is added to an oxidized fat sample that contains fat peroxides. Fat peroxide, an oxidizing agent, quantitatively liberates iodine ($I_2$) from an acid solution containing iodide ions and little or no water. That is, the quantity of iodine produced is equivalent to the quantity of peroxides present in the sample. The liberated iodine is then titrated with a standardized thiosulfate solution. The number of equivalents of thiosulfate consumed is equal to the number of equivalents of iodine produced, which in turn is equal to the number of equivalents of peroxides present in the sample. Starch is added to the solution to indicate the end point of the reaction. Starch adsorbs the iodine on its surface to provide a blue color. The liquid changes from blue to colorless when the last trace of iodine, $I_2$, has been reduced to the iodide ion, $I^-$.

The iodometric AOCS method is time-consuming because it requires the fresh preparation and standardization of reagents and a difficult titration. Trained laboratory personnel are also required to perform the test whose procedures are highly empirical. Any variation in procedure can result in variation in results.

Several colorimetric versions of the iodometric method have been developed to avoid the difficulties of titration. Here, the liberated iodine is measured either directly by means of the absorbance of the triiodide ion ($I_3^-$) in the UV or by measurement of the blue color of the starch-iodine complex. Spectrophotometry and infrared spectroscopy have been utilized. These tests accurately measure the degree of fat oxidation but they also require technical personnel and equipment.

Based on the same iodometric method, U.S. Pat. No. 4,098,575 discloses an assay for peroxide value using a "PV test paper". A predetermined amount of oil is placed on a test paper that is impregnated with a starch and potassium iodide solution to liberate iodine. A predetermined amount of water is placed on the test paper to cause the blue color to appear. The use of a "PV test sheet" has also been reported [Asakawa et al., 1980, in *Autoxidation in Food and Biological Systems*, Simic, M. and M. Karel (eds.), Plenum Press, New York, pp 185–190]. The method is basically the same test for peroxide value as the PV test paper except that a silica gel TLC chromatograph sheet is used. However, these tests are again not simple because the "PV test paper or sheet" has to be prepared. The use of only liquid reagents appeared desirable.

The use of a "PV test solution" to determine peroxides in dried foods has also been reported [Asakawa, 1980, in *Autoxidation in Food and Biological Systems*, Simic, M. and M. Karel (eds.), Plenum Press, New York, pp 185–190]. The test solution consists of ethyl alcohol, ethyl cellosolve and potassium iodide. The dried food sample is placed in the test solution and then taken out to dry. When the dried sample is placed in water, blue color develops at the cut end or on the surface of the dried food. The disadvantage of this test is that it is limited to dried foods and cannot be used with solid or liquid fat.

Diagnostic test kits are available that visually evaluate the quality of discarded frying oil and are used at restaurants and food-service institutions (Al-Kahtani, 1991, *J. Amer. Oil Chem. Soc.*, 68(11): 857–862). These products measure free fatty acids and total alkaline materials (soaps), but not peroxide value. Another similar test kit that is simple to use is an environmental test kit that measures hydrogen peroxide in water. However, that kit is not useful for oleaginous samples.

The feed or food processor requires a quick and easy assay and test kit to qualitatively measure the amount of fat oxidation at the processor's loading dock or train siding. The disclosures that follow describe one such assay and test kit.

BRIEF SUMMARY OF THE INVENTION

It has now been found that a very quick, easy and simple assay to determine the acceptability of fat such as that received for processing can be performed by even non-technical personnel in the field. The assay qualitatively determines whether a fat sample contains an amount of peroxides that are above or below a predetermined peroxide value. A sample having a value below the predetermined peroxide value is considered to be of acceptable fat quality, whereas a sample having a value above that predetermined value is considered unacceptable. Values above the predetermined peroxide value result in a visible color change in the assay so that a rapid and easy determination can be made by a processor to accept or reject fat received.

A process of the invention is based on the iodometric method. A predetermined weight of fat to be assayed is dissolved in a first reagent solution of a predetermined amount of a 3:2 volume:volume solution of acetic acid-:isooctane that contains a dispersing amount of a surfactant, preferably sodium lauryl sulfate, to form a first organic solution.

A second reagent solution of saturated potassium iodide that is preferably stabilized with a water-soluble alkaline material, preferably sodium hydroxide, is added to the dissolved fat to form a second organic solution. The second organic solution is agitatingly admixed for a time period, preferably one minute, sufficient for the iodide ions to react with fat peroxides that may be present. The amount of potassium iodide used is sufficient to provide an amount of iodide ions in excess of those needed to react with a predetermined amount of peroxides that may be present in the oxidized fat sample to form iodine.

A third reagent composition comprising a starch indicator dispersion in an aqueous iodine reductant solution is then agitatingly admixed with the second organic solution to form a two phase aqueous/organic composition. The sodium thiosulfate is present in an amount sufficient to reduce only the amount of iodine formed from a predetermined amount of fat peroxides that provide a peroxide value that is acceptable for the amount of fat used. Any excess or unreacted iodine reacts with the starch to form an aqueous phase having other than a yellow or colorless color, e.g. blue or burgundy, indicating that the amount of peroxides in the fat sample is greater than an acceptable amount.

The process of the invention also permits the use of a simple test kit to rapidly assay for an unacceptable amount of oxidized fat in a fat sample. A test kit includes a first container that contains a predetermined amount of a 3:2 volume:volume solution of acetic acid:isooctane and a dispersing amount of a surfactant, preferably sodium lauryl sulfate. This solution is present in an amount sufficient to dissolve a predetermined weight of fat of a fat sample. A second kit container contains a volume of a saturated solution of potassium iodide that is preferably stabilized with a stabilizing amount of a water-soluble alkaline material, preferably sodium hydroxide. This solution is present in a volume sufficient to provide an amount of iodide ions needed to react with fat peroxides in excess of a predetermined fat peroxides amount and form iodine. A third kit container contains an aqueous starch indicator dispersion in a predetermined amount of aqueous iodine reductant, preferably sodium thiosulfate, solution whose amount is sufficient to reduce only an amount of iodine formed from a predetermined amount of fat peroxides present in the predetermined fat weight and having peroxide value that is equal to or less than a predetermined PV.

The present invention has several benefits. It provides a rapid and simple assay for the processor to determine the acceptability of a fat shipment on the loading dock or train siding. Its assay is readily performed in the field even by non-technical personnel and provides rapid results. The assay is easy to carryout in that it only requires the mixing of three different ready-made reagent solutions with the fat sample. The end-point is a visible color change that enables a rapid determination to be made by a processor to accept or reject an incoming fat shipment. A test kit of the invention is convenient and easy to use.

BRIEF DESCRIPTION OF THE DRAWINGS

FIG. 1 illustrates a test kit of the present invention.

DETAILED DESCRIPTION OF THE INVENTION

The present invention provides an assay that is useful for a qualitative but not a quantitative determination of fat oxidation. A process of the invention uses a visible color change to show whether a fat sample contains an amount of fat peroxides above or below that which produces a predetermined peroxide value. The predetermined peroxide value (PV) can be any peroxide value depending on the fat or oil quality desired by the processor.

In the preferred embodiment, which is designed for the animal feed processor, PV=5. A peroxide value below 5 indicates that the fat is of acceptable quality, whereas a value above 5 indicates that the fat is unacceptable. The process of the invention provides rapid results by use of a technique that is much simpler than the AOCS method.

A test kit of the present invention contains premeasured quantities of reagents in amounts sufficient to carry out at least one assay. Each of three reagent solutions is contained within its own container. A preferred embodiment of a contemplated test kit utilizes a capped glass vial containing 50 ml of Reagent 1, a disposable polyethylene tuberculin syringe with a syringe cap containing 0.5 ml of Reagent 2, and another capped glass vial containing 30.75 ml of Reagent 3. Each of these reagents is used in its entirety along with 5.00±0.01 grams of fat sample. These reagent solutions can be prepared by means conventional in the art.

Reagent 1 is a predetermined amount (about 50 ml) of a 3:2 volume:volume solution of acetic acid:isooctane with a dispersing amount of a surfactant, preferably a sulfate-containing synthetic surfactant such as sodium lauryl sulfate, present at about 0.05 to about 1 percent by weight, and preferably about 0.1 to about 0.2 weight percent. The above amount of Reagent 1 contains a sufficient amount of isooctane (density=0.72) to dissolve 5.00±0.01 grams of fat sample and enough acetic acid (density=1.05 g/ml) to provide the acidic environment required for the iodometric reactions to occur.

Additional useful surfactants include anionic, cationic, zwitterionic and nonionic surfactants. Examplary anionic sulfate-containing synthetic surfactants include other sodium $C_{12}$–$C_{16}$ sulfates such as sodium cetyl sulfate and sodium stearyl sulfate, the sodium nonoxynol-(4–10) sulfates such as sodium nonoxynol-(4) sulfate, and sodium nonoxynol-(8) sulfate, and the sodium octoxynol-(6 or 8) sulfates. Sodium lauryl sulfate is preferred. Exemplary cationic surfactants include myristyl dimethyl benzyl ammonium chloride, lauryl dimethyl benzyl ammonium chloride, cetyl dimethyl benzyl ammonium chloride and the like. Exemplary zwitterionic surfactants include lecithin, lauryl betain and the like. Exemplary nonionic surfactants include ethers of a $C_{12}$–$C_{16}$ alcohol and 2–10 moles of polyethyleneglycol such as polyethyleneglycol (3) tridecyl ether, polyethyleneglycol (4) oleyl ether, polyethyleneglycol (10) cetyl ether.

Reagent 2 is a solution of saturated potassium iodide that is present in an amount sufficient to provide an amount of iodide ions to react with the fat peroxides of the fat sample to form iodine. The volume of Reagent 2 used is predetermined to provide an amount of iodide ions in excess of those needed to react with an acceptable amount of fat peroxides present in a fat sample so that an unacceptable amount of fat peroxides that provide a PV greater than a predetermined value can be detected. Put differently, the volume of saturated potassium iodide solution used is sufficient to provide an amount of iodide ions needed to react with fat peroxides present in excess of a predetermined fat peroxides amount. The volume of saturated potassium iodide solution utilized can vary with the amount of fat sample used and the predetermined PV.

Reagent 2 is preferably stabilized by a stabilizing amount of a water-soluble alkaline material, preferably sodium hydroxide. The amount used is typically about 0.5 to about 1.5 g/kg of saturated KI solution. Other alkaline materials such as the inorganic alkalis, potassium hydroxide, calcium hydroxide, and magnesium hydroxide can also be used. Reagent 2 is preferably prepared using de-ionized water such as that in which dissolved ions have been removed by reverse osmosis or an ion exchange resin. Reagent 2 is preferably packaged in a container that does not permit ready access to air or light. The above-noted syringe provides one such container.

Reagent 3 contains an aqueous composition of a starch indicator dispersion in an iodine reductant solution such as a sodium thiosulfate solution. Other useful iodine reductants include tin(III) tartrate, tin(II) chloride, sodium sulfite and sodium hydrogen sulfite, with sodium thiosulfate being preferred.

The starch indicator dispersion is a starch dispersion, preferably potato starch, in distilled water. Any starch that forms a colored adduct with iodine can be used. The amount of starch is not critical although too much can lead to turbidity and too little can lead to difficulty in determining assay results. The starch can be used in an amount of about 1 to about 50 g/liter, with an amount of about 16 g/liter being preferred and convenient.

The iodine reductant such as the preferred sodium thiosulfate is present in an amount that is sufficient to reduce only an amount of iodine formed from a predetermined amount of fat peroxides present in the fat sample. The sodium thiosulfate or other reductant solution is therefore of variable volume and concentration, and the amount used depends on the predetermined peroxide value. For the preferred embodiment in which PV=5 that utilized 5.00±0.01 grams of fat, Reagent 3 is a composition prepared by the admixture of 30 ml of distilled or deionized water, 0.5 ml of starch indicator dispersion (0.01 g/liter) and 0.25 ml of 0.1 N sodium thiosulfate solution. Reagent 3 is also preferably prepared using de-ionized water, and is also contained in a container that limits access of oxygen to the solution.

The amount of exemplary sodium thiosulfate required for determining other predetermined peroxide values can be determined from the following equation:

$$\text{mL Na}_2\text{S}_2\text{O}_3 = \frac{\text{Normality of Na}_2\text{S}_2\text{O}_7 \times 1000}{\text{Sample Weight} \times PV \text{ in } meq/\text{kg}}$$

The reagent solutions are not limited to the above-described ingredients. Other materials can be present in the test solutions such as stabilizers for the sodium thiosulfate solution or the starch indicator solution. An instruction sheet is also preferably included in the kit.

A process of the present invention comprises the steps of sequentially admixing predetermined amounts of the three ready-made reagent solutions (Reagents 1, 2 and 3) with a predetermined amount of a fat sample. The fat can be solid or liquid. The mixing can take place in any suitable transparent mixing apparatus, preferably a 125 ml Erlenmeyer flask.

Thus, for example, a weighed sample of fat is placed in a 125 ml Erlenmeyer flask. The weight of the fat sample for the preferred embodiment is 5.00±0.01 grams, but can be in the range of 0.10 to 20.00 grams. A change in the weight of the fat sample requires a proportional change in the amount of reagent solutions used, and the lower the weight of the fat sample the lower is the accuracy of the assay process.

Reagent 1 is added into the flask, and the contents are swirled until the fat is dissolved. Reagent 2 is then added into the flask, the admixture swirled, and the resulting second organic solution is maintained with agitation, as by occasional swirling, for a predetermined time sufficient for any fat peroxides present in the fat to react with the iodide ions to form iodine. For the preferred reagents described here, a maintenance time of one minute is used. The surfactant in Reagent 1 aids in dispersing the fat to keep the fat in contact with the iodide ions.

One minute is the standard time used in peroxide value determinations for the iodide ions to react with the peroxides to form iodine. It is therefore critical to maintain the solution for exactly one minute in order for the result to be comparable to the AOCS and other iodometric methods. However, other time periods such as 0.5 to 5.0 minutes can be used.

Reagent 3 is then added into the flask, and the contents are swirled vigorously to form a two-phase, aqueous/organic composition. The surfactant in Reagent 1 also aids in the contacting of the two phases, while not forming an emulsion.

The sodium thiosulfate present in Reagent 3 reduces only an amount of iodine formed from a predetermined (e.g. acceptable) amount of peroxides present in the fat sample. Any excess or unreacted iodine reacts with the starch indicator to form a blue or burgundy color, indicating that the amount of peroxides in the fat sample is above the predetermined peroxide value. If the peroxide value is above the predetermined peroxide value; i.e. where an unacceptable level of peroxides is present in a fat sample, the lower phase in the flask is blue or burgundy. If the peroxide value is below the predetermined peroxide value, the lower phase is colorless or yellow. An equivocal result, where the aqueous phase is neither blue/burgundy nor colorless/yellow, is deemed to be positive. Thus, the amount of fat peroxides in the sample is greater than the predetermined amount when the aqueous phase is other than yellow or colorless.

A process of the present invention differs from a process of the AOCS assay method in a number of respects. For example, here, only an amount of thiosulfate is used that equals the predetermined peroxide value, and that amount is added to the reaction mixture in a single admixture (bolus) as compared to dropwise or titermetric addition in the AOCS method.

In addition, here, there is no titration to a finicky end point as in the AOCS method. Rather, once the two phase aqueous/organic composition is obtained, one need merely look at the color of the lower, aqueous phase to determine an answer; i.e., an other than colorless or yellow solution indicates that the fat sample contained fat peroxides in excess of the predetermined amount.

Third, iodine can react with unsaturation present in fats, and as such, the time of contact between any iodine formed and the fat should be minimized. In a process of the present invention, the only times required are the maintenance time for the initial iodine formation, typically one minute, and the time required for admixture of the thiosulfate solution bolus, typically a few seconds. In the AOCS method, the final titration can take several minutes, and permit reaction between any fat unsaturation present and produced iodine.

No special conditions are necessary for carrying out the process steps of the present invention. Thus, a process of the invention can be performed at ambient conditions. However, other conditions can be used so long as they do not unexpectedly change the reactions that ordinarily occur using predetermined amounts of the reagent solutions and fat sample.

A process of the present invention has been found to provide results that correlate very well with the AOCS Method referred to above. This process has been shown to reliably indicate whether a fat sample is of acceptable or unacceptable quality without the need for complex and lengthy laboratory testing.

The following examples are given to illustrate the invention, but are not deemed to be limiting thereof.

EXAMPLE 1

Laboratory Fat Sample Assay

The following reagent solutions were prepared to assay various fat samples at PV=5:

1. Reagent 1 was prepared by mixing three volumes of reagent-grade glacial acetic with two volumes of reagent-grade isooctane to form Solution A. One gram of sodium lauryl sulfate was added and dispersed per liter of Solution A.

2. Reagent 2 was prepared by mixing a saturated solution of potassium iodide and 0.1 gram sodium hydroxide per 100 grams of saturated KI solution. The saturated potassium iodide was prepared by dissolving an excess of potassium iodide in distilled water (1 gram dissolves in 0.7 ml of water).

3. Reagent 3 was prepared by mixing 30 ml distilled water, 0.5 ml of starch indicator solution (16.3 g/liter) and 0.25 ml of 0.1 N sodium thiosulfate solution.

Five fat samples prepared in the laboratory were assayed at ambient temperature and pressure using AOCS Method Cd 8b-90 and a process of the present invention (Quick Test). Each fat sample weighing 5.00±0.01 grams was placed in a 125 ml Erlenmeyer flask. Reagent 1 (50 ml) was added into the flask and swirled until the fat was dissolved. Reagent 2 (0.5 ml) was added, swirled, and held for exactly one minute with occasional swirling of the flask. After exactly one minute, Reagent 3 (30.75 ml) was added into the flask and swirled vigorously to form a two-phase solution. The sodium thiosulfate in Reagent 3 was in an amount sufficient to cause a color change at PV=5. If the lower phase in the flask was blue or burgundy, the assay was positive, and the fat was deemed unacceptable (above PV of 5). If the lower phase in the flask was colorless or yellow, then the test was negative, and the fat was deemed acceptable (below PV of 5). The results of these assays are depicted in Table 1, below.

TABLE 1

| Sample | Quick Test | AOCS Method (meq/kg) |
| --- | --- | --- |
| 1 | + | 52.2 |
| 2 | + | 6.0 |
| 3 | +(?) | 5.4 |
| 4 | − | 4.8 |
| 5 | − | 0.0 |

As is seen, the Quick Test assay of this invention provided fast and accurate qualitative assays for the various samples. The resulting color of Sample 4 was between a very light blue or a discolored yellow, thereby providing a positive result inasmuch as the aqueous phase was not clearly yellow or colorless.

2: Rendering Plant Fat Sample Assay

Six fat samples that were obtained from a rendering plant were assayed using AOCS Method Cd 8b-90 and the Quick Test process of the present invention as in Example 1. The results of this assay are depicted in Table 2.

TABLE 2

| Sample | Quick Test | AOCS Method (meq/kg) |
| --- | --- | --- |
| 1 | + | 18.8 |
| 2 | − | 1.4 |
| 3 | − | 1.2 |
| 4 | − | 1.2 |
| 5 | − | 1.6 |
| 6 | − | 1.0 |

As is again seen from the above results, an assay of the present invention provided results that were in complete agreement with results provided by the more rigorous AOCS assay method. That agreement was, however, obtained in much less time.

The foregoing description and the examples are intended as illustrative and are not to be taken as limiting. Still other variations within the spirit and scope of this invention are possible and will readily present themselves to those skilled in the art.

we claim:

1. A test kit for determining whether a fat sample contains peroxides in an amount above a predetermined fat peroxides amount that comprises:

(a) a first container having a first reagent comprising a 3:2 volume:volume solution of acetic acid:isooctane and a dispersing amount of a surfactant, said first reagent being sufficient to dissolve a predetermined weight of fat in said fat sample;

(b) a second container containing a predetermined volume of a saturated aqueous solution of potassium iodide, said solution volume being sufficient to provide an amount of iodide ions needed to react with fat peroxides present in the fat in excess of a predetermined fat peroxides amount to form iodine; and (c) a third container containing an aqueous composition of starch indicator dispersed in a predetermined amount of iodine reductant solution, the amount iodine reductant being sufficient to reduce only an amount of iodine formed from a predetermined amount of fat peroxides present in the fat in said fat sample.

2. The test kit according to claim 1 wherein said surfactant is sodium lauryl sulfate.

3. The test kit according to claim 1 wherein said saturated aqueous solution potassium iodide further contains a stabilizing amount of a soluble alkaline material.

4. The test kit according to claim 3 wherein said soluble alkaline material is sodium hydroxide.

5. The test kit according to claim 1 wherein said iodine reductant is sodium thiosulfate.

* * * * *